US012213751B1

(12) United States Patent
Toledano et al.

(10) Patent No.: US 12,213,751 B1
(45) Date of Patent: Feb. 4, 2025

(54) INTERACTIVE GUIDANCE OF DENTAL IMPLANT SURGERY

(71) Applicant: Mars Dental AI Ltd., Beit Yitzhak-ShaAr Hefer (IL)

(72) Inventors: Eyal Toledano, Beit Yitzhak Shaar-Hefer (IL); Eyal Tsvi Zak, Kibbutz Megiddo (IL); Ariel Shusterman, Kiriyat Tivon (IL)

(73) Assignee: Mars Dental AI Ltd., Beit Yitzhak-ShaAr Hefer (IL)

( * ) Notice: Subject to any disclaimer, the term of this patent is extended or adjusted under 35 U.S.C. 154(b) by 0 days.

(21) Appl. No.: 18/656,634

(22) Filed: May 7, 2024

(51) Int. Cl.
*A61B 34/20* (2016.01)
*A61B 34/00* (2016.01)
*A61B 90/00* (2016.01)
*A61C 1/08* (2006.01)
*A61C 8/00* (2006.01)

(52) U.S. Cl.
CPC .............. *A61B 34/25* (2016.02); *A61B 34/20* (2016.02); *A61B 90/37* (2016.02); *A61B 90/39* (2016.02); *A61C 1/084* (2013.01); *A61C 8/0089* (2013.01); *A61B 2090/365* (2016.02); *A61B 2090/372* (2016.02)

(58) Field of Classification Search
CPC ......... A61B 34/25; A61B 34/20; A61B 90/37; A61C 1/084; A61C 8/0089
USPC ....................................................... 715/708
See application file for complete search history.

(56) References Cited

U.S. PATENT DOCUMENTS

| | | | |
|---|---|---|---|
| 5,688,118 A | 11/1997 | Hayka et al. | |
| 7,367,801 B2 | 5/2008 | Saliger | |
| 7,457,443 B2 * | 11/2008 | Persky | A61C 1/084 348/66 |
| 10,064,700 B2 | 9/2018 | Fudim | |
| 11,051,914 B2 | 7/2021 | Kopelman | |
| 11,357,576 B2 | 6/2022 | Jo et al. | |
| 11,399,915 B2 | 8/2022 | Colby | |
| 11,510,638 B2 | 11/2022 | Merritt | |

(Continued)

FOREIGN PATENT DOCUMENTS

WO WO 2022/190105 9/2022

OTHER PUBLICATIONS

Notice of Allowance Dated Jul. 23, 2024 From the US Patent and Trademark Office Re. U.S. Appl. No. 18/656,633. (10 Pages).

(Continued)

*Primary Examiner* — William D Titcomb

(57) ABSTRACT

There is provided, an interactive graphical user interface (GUI), comprising: presenting within the GUI, a first overlay of a target virtual vector overlaid on an image(s) of an oral cavity of a subject captured by an image sensor during a dental session of the subject, wherein the target virtual vector denotes a target vector defining a target location and/or a target angle for drilling by a real-world bur of a real-world drill for insertion of a dental implant, monitoring a real-world location and/or angle of the real-world bur of the drill during manipulations by a user, and dynamically updating, within the GUI, a second overlay of a current virtual vector overlaid on the image(s) including the first overlay, the current virtual vector including a virtual location and/or virtual angle corresponding to a current value of the monitored real-world location and/or angle of the real-world bur of the drill.

22 Claims, 7 Drawing Sheets

(56) References Cited

U.S. PATENT DOCUMENTS

| | | | |
|---|---|---|---|
| 11,559,377 B2 | 1/2023 | Kopelman et al. | |
| 11,594,002 B2 | 2/2023 | Coustaud et al. | |
| 11,684,374 B2 | 6/2023 | Kang et al. | |
| 11,727,581 B2 | 8/2023 | Lang | |
| 11,730,564 B2 | 8/2023 | Colby | |
| 11,751,944 B2* | 9/2023 | Lang | A61B 90/37 |
| | | | 606/130 |
| 11,771,533 B2 | 10/2023 | Senn et al. | |
| 11,931,114 B2* | 3/2024 | Qian | A61B 34/25 |
| 11,978,203 B2 | 5/2024 | Kim et al. | |
| 12,053,247 B1* | 8/2024 | Chiou | G06F 3/011 |
| 2011/0045432 A1* | 2/2011 | Groscurth | A61C 9/00 |
| | | | 433/75 |
| 2013/0172731 A1* | 7/2013 | Gole | A61B 6/506 |
| | | | 600/424 |
| 2013/0302752 A1* | 11/2013 | Schneider | A61C 1/084 |
| | | | 433/214 |
| 2013/0309628 A1* | 11/2013 | Orth | A61C 1/084 |
| | | | 433/173 |
| 2014/0186794 A1* | 7/2014 | Deichmann | A61B 5/489 |
| | | | 433/75 |
| 2014/0272773 A1* | 9/2014 | Merritt | A61B 6/512 |
| | | | 433/29 |
| 2015/0150655 A1* | 6/2015 | Frank | A61B 6/5247 |
| | | | 433/29 |
| 2015/0296184 A1* | 10/2015 | Lindenberg | H04N 7/18 |
| | | | 348/77 |
| 2016/0135904 A1* | 5/2016 | Daon | A61B 5/064 |
| | | | 600/424 |
| 2016/0235481 A1* | 8/2016 | Dorman | A61B 17/1707 |
| 2018/0008355 A1* | 1/2018 | Mozes | A61C 1/0015 |
| 2018/0168781 A1* | 6/2018 | Kopelman | A61B 34/10 |
| 2019/0038367 A1* | 2/2019 | Ciriello | A61B 90/361 |
| 2019/0269482 A1* | 9/2019 | Shanjani | A61B 90/37 |
| 2019/0350680 A1* | 11/2019 | Chekh | G06T 15/83 |
| 2020/0008877 A1* | 1/2020 | Jo | A61C 9/0053 |
| 2020/0138518 A1 | 5/2020 | Lang | A61B 90/37 |
| 2021/0161626 A1* | 6/2021 | Kim | A61C 13/0001 |
| 2021/0186454 A1* | 6/2021 | Behzadi | A61B 7/023 |
| 2021/0192759 A1* | 6/2021 | Lang | A61B 90/98 |
| 2022/0015875 A1 | 1/2022 | Palmer | |
| 2022/0047278 A1* | 2/2022 | Fitz | A61F 2/38 |
| 2022/0084267 A1 | 3/2022 | Ezhov et al. | |
| 2022/0257332 A1* | 8/2022 | Duong | A61C 1/084 |
| 2022/0287676 A1* | 9/2022 | Steines | A61B 6/102 |
| 2022/0361992 A1 | 11/2022 | Ezhov et al. | |
| 2023/0252748 A1 | 8/2023 | Ezhov et al. | |
| 2023/0298272 A1 | 9/2023 | Ezhov et al. | |
| 2023/0414318 A1 | 12/2023 | Colby | |
| 2023/0419631 A1 | 12/2023 | Ezhov et al. | |
| 2024/0041530 A1 | 2/2024 | Lang | |
| 2024/0046490 A1 | 2/2024 | Lang | |
| 2024/0148469 A1 | 5/2024 | Colby | |

OTHER PUBLICATIONS

Second Notice of Allowance Dated Oct. 16, 2024 together with Interview Summary From the US Patent and Trademark Office Re. U.S. Appl. No. 18/656,633. (18 Pages).

* cited by examiner

INTERACTIVE GUIDANCE OF DENTAL IMPLANT SURGERY

RELATED APPLICATIONS

This application is related to co-filed U.S. Patent Application entitled "INTERACTIVE VISUALIZATION OF DENTAL IMPLANT POSITION PLANNING" 18656633, the contents of which are incorporated herein by reference in their entirety.

This application is also related to International Patent Application No. PCT/IL2022/050274, having Publication No. WO2022/190105, entitled "ENHANCING DENTAL VIDEO TO CT MODEL REGISTRATION AND AUGMENTED REALITY AIDED DENTAL TREATMENT", filed on Mar. 10, 2022, incorporated herein by reference in its entirety.

BACKGROUND

The present invention, in some embodiments thereof, relates to user interfaces and, more specifically, but not exclusively, to a user interface for use during a dental procedure.

User interface technologies have dramatically evolved in recent times and have spread to numerous applications, uses and practices. Among other applications, the use of user interfaces to support dental procedures has also dramatically increased, in particular for more complex dental procedures such as, for example, dental surgery, dental implants and/or the like.

SUMMARY

According to a first aspect, an interactive graphical user interface (GUI) for guiding positioning of a dental implant in a subject, comprises: presenting within the GUI, a first overlay of a target virtual vector overlaid on at least one image of an oral cavity of a subject captured by at least one image sensor during a dental session of the subject, wherein the target virtual vector denotes a target vector defining a target location and/or a target angle for drilling by a real-world bur of a real-world drill for insertion of a dental implant, monitoring a real-world location and/or angle of the real-world bur of the drill during manipulations by a user, and dynamically updating, within the GUI, a second overlay of a current virtual vector overlaid on the at least one image including the first overlay, the current virtual vector including a virtual location and/or virtual angle corresponding to a current value of the monitored real-world location and/or angle of the real-world bur of the drill.

According to a second aspect, a system for presenting an interactive graphical user interface (GUI) for guiding positioning of a dental implant in a subject, comprises: at least one processor executing a code for: presenting a first overlay of a target virtual vector overlaid on at least one image of an oral cavity of a subject captured by at least one image sensor during a dental session of the subject, wherein the target virtual vector denotes a target vector defining a target location and/or a target angle for drilling by a real-world bur of a real-world drill for insertion of a dental implant, monitoring a real-world location and/or angle of the real-world bur of the drill during manipulations by a user, and dynamically updating a second overlay of a current virtual vector overlaid on the at least one image including the first overlay, the current virtual vector including a virtual location and/or virtual angle corresponding to a current value of the monitored real-world location and/or angle of the real-world bur of the drill.

According to a third aspect, a non-transitory medium storing program instructions for presenting an interactive graphical user interface (GUI) for guiding positioning of a dental implant in a subject, which when executed by at least one processor, cause the at least one processor to: present a first overlay of a target virtual vector overlaid on at least one image of an oral cavity of a subject captured by at least one image sensor during a dental session of the subject, wherein the target virtual vector denotes a target vector defining a target location and/or a target angle for drilling by a real-world bur of a real-world drill for insertion of a dental implant, monitor a real-world location and/or angle of the real-world bur of the drill during manipulations by a user, and dynamically update a second overlay of a current virtual vector overlaid on the at least one image including the first overlay, the current virtual vector including a virtual location and/or virtual angle corresponding to a current value of the monitored real-world location and/or angle of the real-world bur of the drill.

In a further implementation form of the first, second, and third aspects, further comprising computing the target virtual vector based on anatomical landmarks identified within the oral cavity and a set of rules applied to distances to the anatomical landmarks.

In a further implementation form of the first, second, and third aspects, further comprising dynamically tracking a misalignment between the current virtual vector and the target virtual vector, and presenting within the GUI, an indication of the misalignment.

In a further implementation form of the first, second, and third aspects, further comprising presenting within the GUI, an indication for reducing the misalignment for obtaining an alignment between the current virtual vector and the target virtual vector.

In a further implementation form of the first, second, and third aspects, the indication for reducing the misalignment is for adapting at least one of: spatial coordinates of the current virtual vector to match the spatial coordinates of the target virtual vector, the angle of the current virtual vector to substantially match the angle of the target virtual vector, and a depth of the current virtual vector corresponding to a tip of the tool relative to an initial location for drilling defined by the target virtual vector.

In a further implementation form of the first, second, and third aspects, further comprising computing a value indicating the amount of misalignment presenting an alert within the GUI when the value is larger than a threshold.

In a further implementation form of the first, second, and third aspects, the current virtual vector and the target virtual vector are presented as two distinct visual elements when misaligned, and the visual elements are overlapping and depicted as a single visual element when aligned.

In a further implementation form of the first, second, and third aspects, the current virtual vector is presented as a first line parallel to a long axis of the bur and as a plurality of first visual elements arranged along a first plane, wherein the first line is a normal to the first plane, and a center of the plurality of first visual elements and a center of the first line correspond to a tip of the bur.

In a further implementation form of the first, second, and third aspects, the target virtual vector is presented as a second line parallel to a direction for drilling for insertion of the dental implant and as a plurality of second visual elements arranged along a second plane, wherein a center of the plurality of second visual elements corresponds to an initial location for drilling, wherein a center of the second line corresponds to the initial location for drilling, wherein a first portion of the second line below the center is depicted within tissue and a second portion of the second line above the center is depicted external to the tissue.

In a further implementation form of the first, second, and third aspects, further comprising: dynamically computing an adaption of the current virtual vector for alignment with the target virtual vector, and visually presenting within the GUI a marker with respect to the plurality of first visual elements indicating the adaption for alignment.

In a further implementation form of the first, second, and third aspects, a location and/or shape and/or color of the marker with respect to the plurality of first visual elements indicates a direction and/or amount and/or angle for adapting the current virtual vector for alignment with the target virtual vector.

In a further implementation form of the first, second, and third aspects, the plurality of first visual elements and the plurality of second visual elements are presented as a plurality of concentric circles, the marker is presented as a thickened and/or colored arc portion of the plurality of concentric circles, and at least one of: a color, length, a specific concentric circle of the plurality of concentric circles, visually indicates the direction and/or amount and/or angle for adapting the current virtual vector for alignment with the target virtual vector.

In a further implementation form of the first, second, and third aspects, the specific concentric circle of the plurality of concentric circles is dynamically adapted according to a magnitude of the misalignment between the current virtual vector and the target virtual vector, wherein a relatively outer concentric circle indicates a relatively larger magnitude and a relatively inner concentric circle indicates a relatively smaller magnitude.

In a further implementation form of the first, second, and third aspects, further comprising: dynamically computing an adaptation vector indicating a magnitude and/or direction for adapting the location of the current virtual vector for alignment with a location of the target virtual vector, and dynamically updating the adaption vector according to monitored changes in location of the current virtual vector.

In a further implementation form of the first, second, and third aspects, the adaption vector is presented as a distance to move along an x-axis, a y-axis, and an amplitude, from the current location of the virtual vector to the location of the target virtual vector.

In a further implementation form of the first, second, and third aspects, the adaption vector is presented as a line connecting a position of the current virtual vector corresponding to a tip of the bur, and a position of the target virtual vector corresponding to an initial location for drilling.

In a further implementation form of the first, second, and third aspects, further comprising: in response to detecting drilling by the drill, terminating the first overlay and the second overlay, and in response to detecting termination of drilling by the drill, re-presenting the first overlay and the second overlay.

In a further implementation form of the first, second, and third aspects, further comprising: detecting a stage of during a procedure for insertion of the dental implant, and setting a presentation protocol of the GUI indicating features for presentation within the GUI according to the stage.

In a further implementation form of the first, second, and third aspects, further comprising: detecting presence of the dental implant and absence of the drill, wherein monitoring is performed for the dental implant instead of the drill, and the current virtual vector corresponds to the dental implant.

In a further implementation form of the first, second, and third aspects, the GUI including first overlay and the second overlay is presented over the at least one image within an augmented reality device worn by a user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
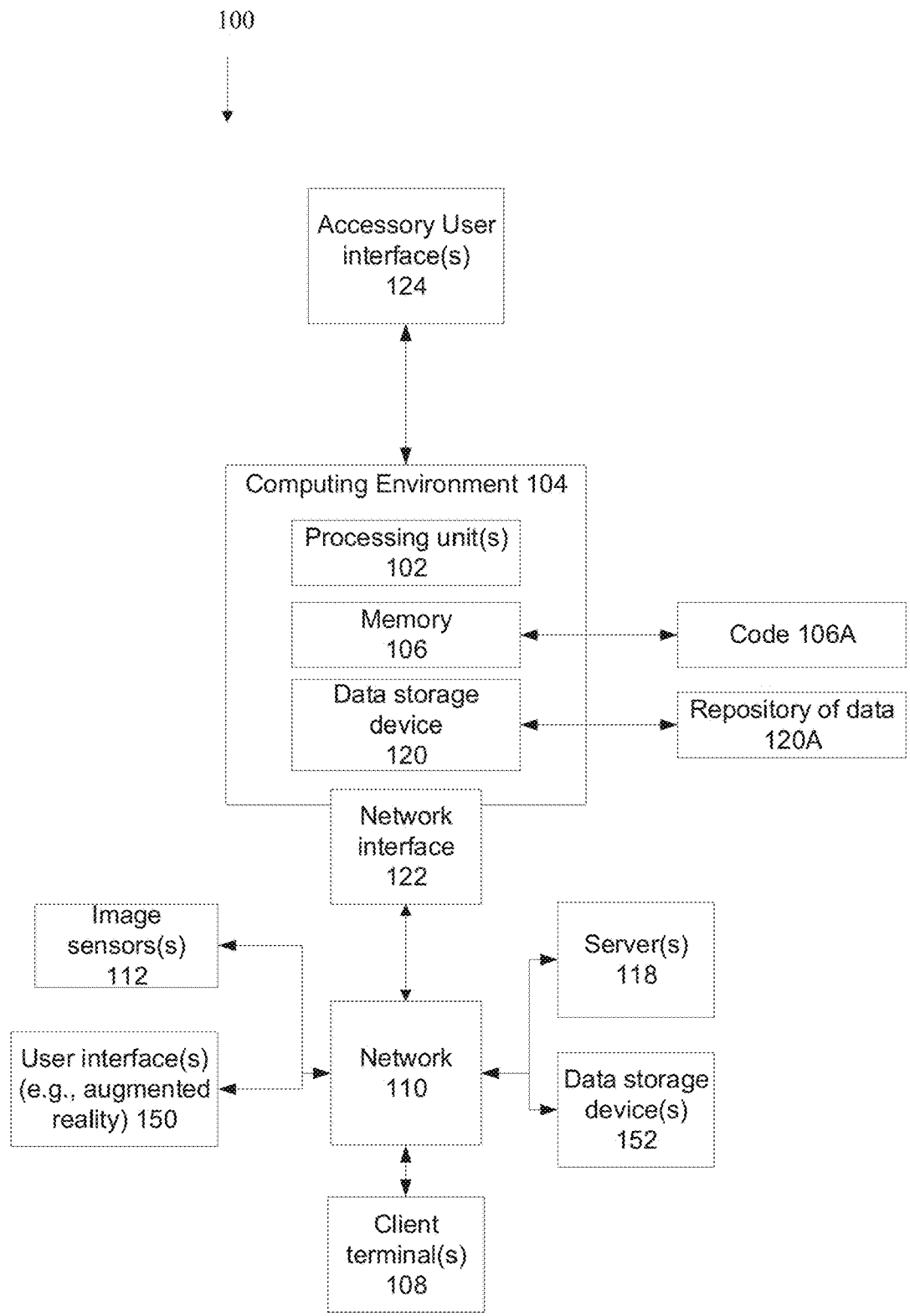
FIG. 1 is a block diagram of components of a system for creating and/or updating a GUI for guiding positioning of a dental implant in a subject, in accordance with some embodiments of the present invention.

The present invention, in some embodiments thereof, relates to user interfaces and, more specifically, but not exclusively, to a user interface for use during a dental procedure.

An aspect of some embodiments of the present invention relates to systems, methods, computing devices, and/or code instructions (stored on a data storage device and executable by one or more processors) for generating and/or updating a user interface, optionally a graphical user interface (GUI) for guiding drilling and/or positioning of a dental implant in a subject, for example, for a dental prosthesis such as a crown. The GUI may be presented within an augmented reality (AR) device worn by a user (e.g., dentist), and/or presented on a display such as for viewing by an assistant to the user (e.g., dental assistant). Sequential frames of an oral cavity of a subject are accessed. The sequential frames are captured by one or more image sensors, such as a camera, optionally installed on the AR device. The sequential frames may be captured during a dental session of the subject for insertion of the dental implant. A target vector is presented over the frames within the GUI, optionally as an overlay. The target virtual vector includes a target vector defining a target location and/or a target angle for drilling by a real-world bur of a real-world drill for insertion of the dental implant. A real-world location and/or real-world angle of the real-world bur of the drill is computed during manipulations by a user (e.g., dentist performing the implant procedure). A current virtual vector including a virtual location and/or virtual angle is computed. The current virtual vector corresponds to the real-world location and/or the real-world angle of the real-world bur. The current virtual vector is dynamically adapted in response to manipulations of the drill by the user. The current virtual vector is presented over the frames, optionally within the overlay or as a second overlay. The current virtual vector may be simultaneously presented with the target virtual vector. The user may user the current virtual vector presented in the GUI to guide real-world manipulations of the drill for drilling at the target virtual vector.

Optionally, an indication of a misalignment between the current virtual vector and the target virtual vector is monitored and/or dynamically computed, and presented within the GUI. Alternatively or additionally, an indication for reducing the misalignment for obtaining an alignment between the current virtual vector and the target virtual vector may be presented within the GUI. The user may use the indication of misalignment and/or the indication for reducing the misalignment to manipulate the drill to position the bur at the physical location within the mount of the subject corresponding to the target virtual vector.

At least one embodiment described herein addresses the technical problem of a user performing the dental implant procedure (e.g., the dentist) needing to know the exact location and angle to drill in order to insert a dental implant. Precise drilling at a specific location and at a specific angle may be important, for example, for optimal placement of the dental implant, minimizing damage to surrounding structures, improving osscointegration, enhancing aesthetic outcomes, reducing risk of implant failure, facilitating prosthetic restoration, and the like.

Some existing dynamic navigation systems direct the dentist by presenting location and angulation information and tracking on a side screen view in 2D. The first view may present location information with concentric circles that are centered around the point of entry. A virtual driller is shown from a top view that is supposed to mimic the real driller top view as tracked by the system. The goal of the dentist is to align the virtual driller to the center of the concentric circles. The second view shows angulation tilt from both buccal-lingual axis (angulation) and the teeth centerline axis (angulation). The dentist needs to use these views in order to locate the driller in the right angle of the planned drilling vector. The third view is a progress bar that tracks the depth of the dill during the procedure. Such existing solutions visualize the navigation directions for the dentist on an external screen (i.e., not at the line of sight), and the decomposed 2D views are disjoint from each other and from the operation of the driller. Therefore, such existing solutions are very complicated for users to learn and operate. These existing solutions are not intuitive and are un-natural for the dentist to use.

At least one embodiment described herein addresses the aforementioned technical problem, and/or improves upon the aforementioned existing approaches, and/or improves upon the aforementioned technical field, by using a previously generated dental plan, for example, automatically computed based on distances and/or directions to nearby anatomical structures (e.g., specific teeth, nerves, roots of teeth, anatomical locations of the jawbone), and/or created as described with reference to U.S. Patent Application entitled "INTERACTIVE VISUALIZATION OF DENTAL IMPLANT POSITION PLANNING" (Ser. No. 18/656,633), for guiding the location and/or angle of the drill. Using the previously generated dental plan, the user is dynamically provided with visual guidance (e.g., instructions) for directing the drill to the correct entry point location and at the correct angulation. The drilling operation may be tracked in real time, in order to verify that the drilling is accurately following the plan and not deviating from the preoperative plan (e.g., depth and/or trajectory).

At least one embodiment described herein addresses the aforementioned technical problem, and/or improves upon the aforementioned existing approaches, and/or improves upon the aforementioned technical field, by generating a single view at the line of sight of the user that includes guidance for both location and angulation and shows the user progress to the correct location and angle. The user is guided by placing one visual element which is fixed, representing the target location and/or angle for drilling, overlaid over another visual element representing the current location and/or angle of the drill. Non-overlap represents misalignment to be corrected by manipulations of the drill. A direct overlap indicates that the drill is at the target location.

At least one embodiment described herein addresses the aforementioned technical problem, and/or improves upon the aforementioned existing approaches, and/or improves upon the aforementioned technical field, by for generating and/or updating a user interface, optionally a graphical user interface (GUI) for guiding drilling and/or positioning of a dental implant in a subject, for example, for a dental prosthesis such as a crown. The GUI may be presented within an augmented reality (AR) device worn by a user (e.g., dentist), and/or presented on a display such as for viewing by an assistant to the user (e.g., dental assistant). A target vector is presented over frames of an oral cavity of the subject captured by a camera during a dental procedure, within the GUI, optionally as an overlay. The target virtual vector includes a target vector defining a target location and/or a target angle for drilling by a real-world bur of a real-world drill for insertion of the dental implant. A real-world location and/or real-world angle of the real-world bur of the drill is computed during manipulations by a user (e.g., dentist performing the implant procedure). A current virtual vector including a virtual location and/or virtual angle is computed. The current virtual vector corresponds to the real-world location and/or the real-world angle of the real-world bur. The current virtual vector is dynamically adapted in response to manipulations of the drill by the user. The current virtual vector is presented over the frames, optionally within the overlay or as a second overlay. The current virtual vector may be simultaneously presented with the target virtual vector. The user may user the current virtual vector presented in the GUI to guide real-world manipulations of the drill for drilling at the target virtual vector. Optionally, an indication of a misalignment between the current virtual vector and the target virtual vector is monitored and/or dynamically computed, and presented within the GUI. Alternatively or additionally, an indication for reducing the misalignment for obtaining an alignment between the current virtual vector and the target virtual vector may be presented within the GUI. The user may use the indication of misalignment and/or the indication for reducing the misalignment to manipulate the drill to position the bur at the physical location within the mount of the subject corresponding to the target virtual vector.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
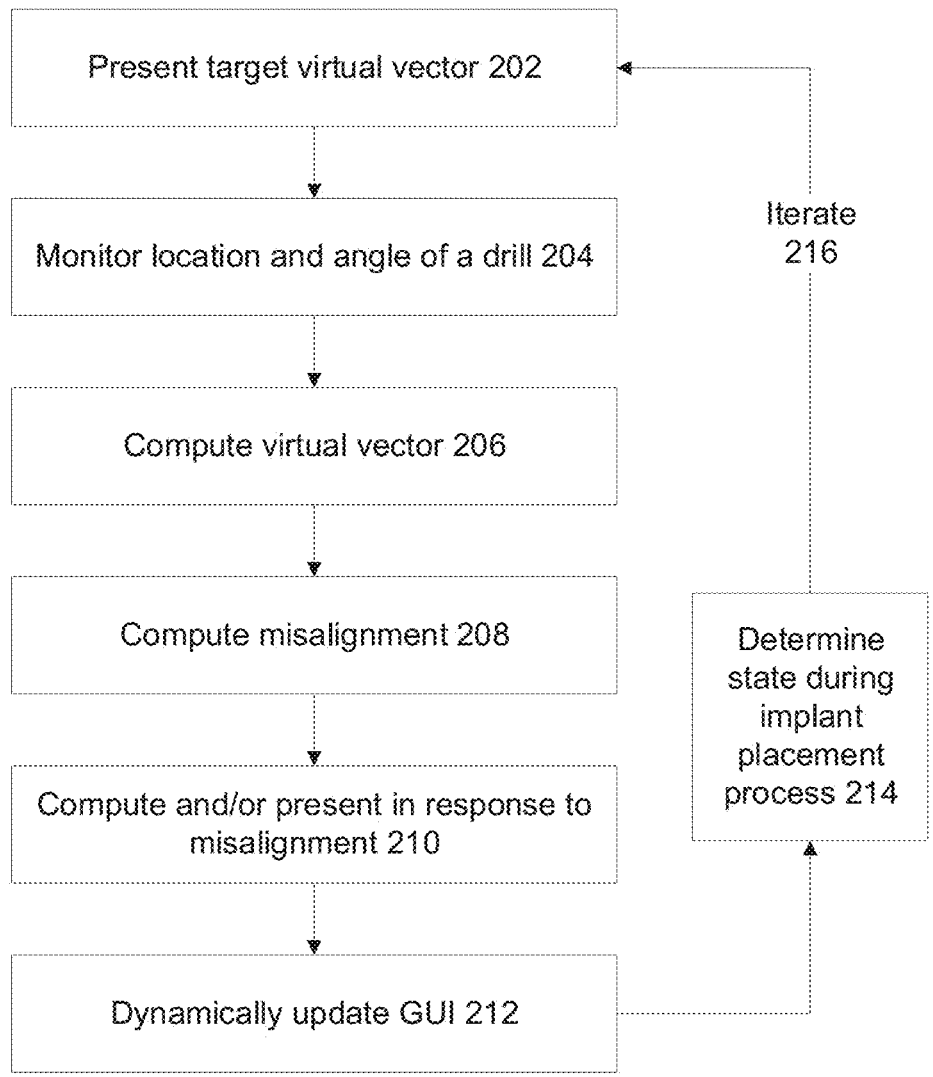
FIG. 2 is a flowchart of a method of creating and/or updating a GUI for guiding positioning of a dental implant in a subject, in accordance with some embodiments of the present invention.
Figure 3:
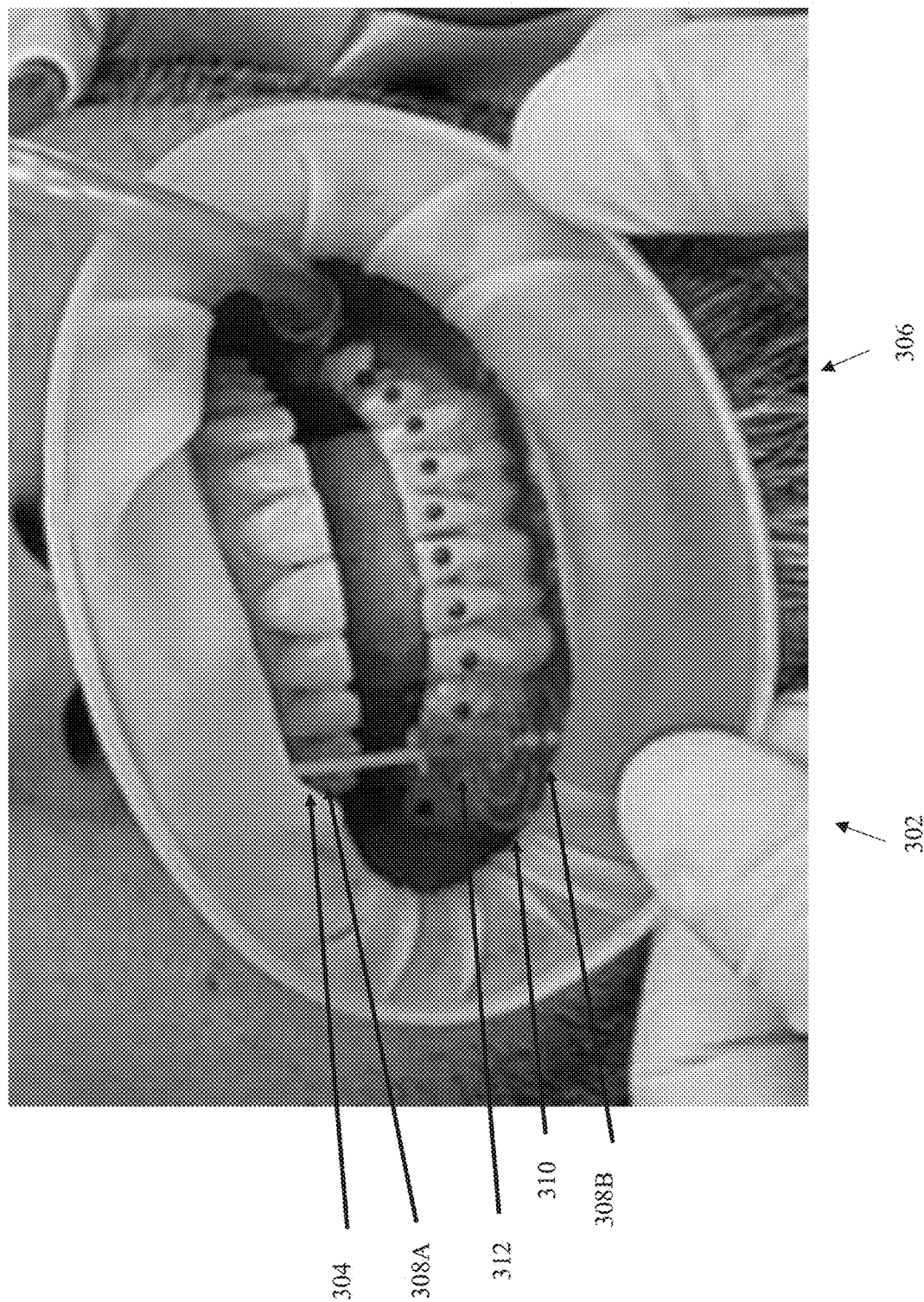
FIG. 3 is a schematic of an exemplary GUI including a target virtual vector overlaid on a frame depicting an oral cavity of a subject, in accordance with some embodiments of the present invention.
Figure 4:
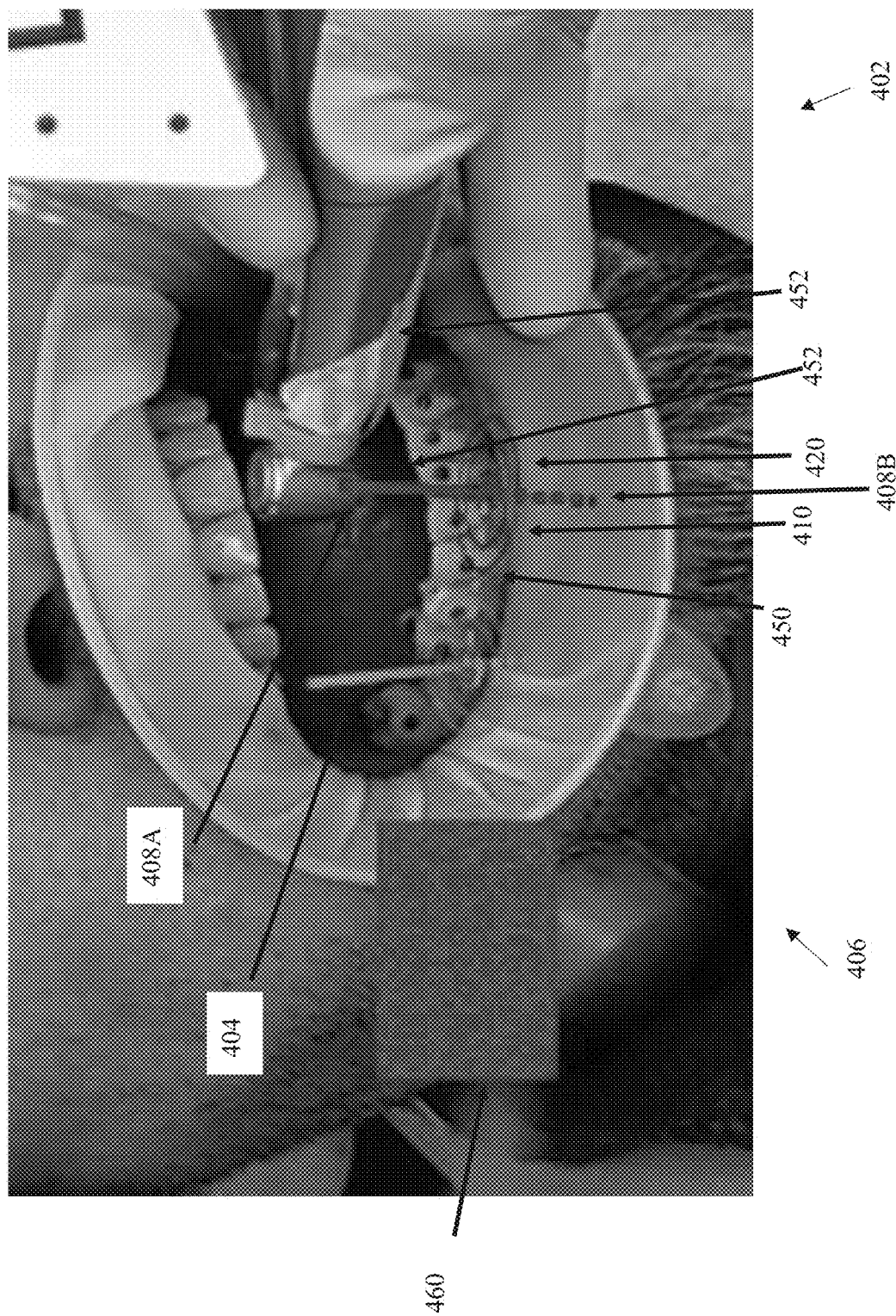
FIG. 4 is a schematic of an exemplary GUI depicting a misalignment between a target virtual vector and a current virtual vector overlaid on a frame depicting an oral cavity of a subject, in accordance with some embodiments of the present invention.
Figure 5:
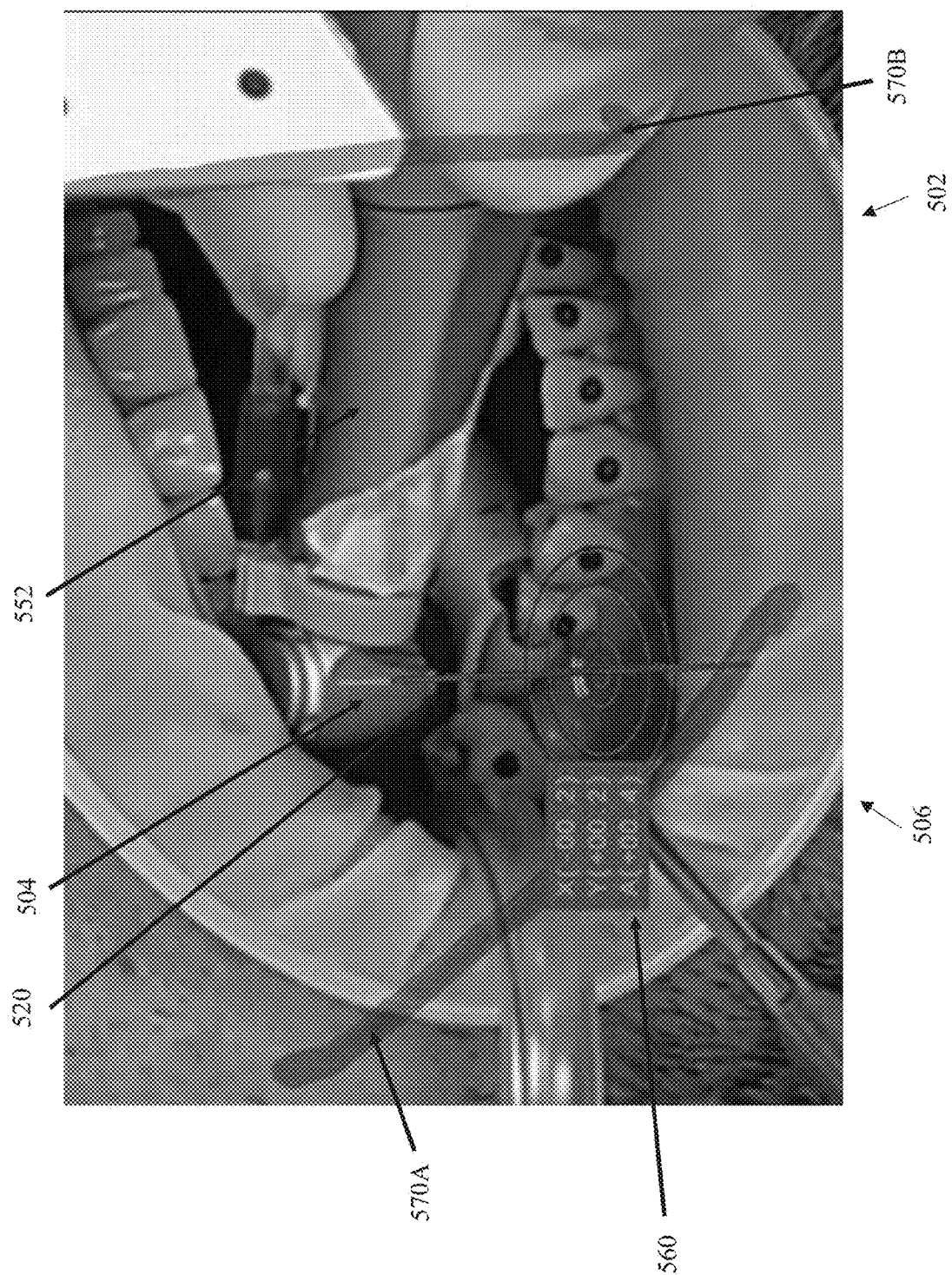
FIG. 5 is a schematic of an exemplary GUI depicting an alignment between a target virtual vector and a current virtual vector overlaid on a frame depicting an oral cavity of a subject, in accordance with some embodiments of the present invention.
Figure 6:
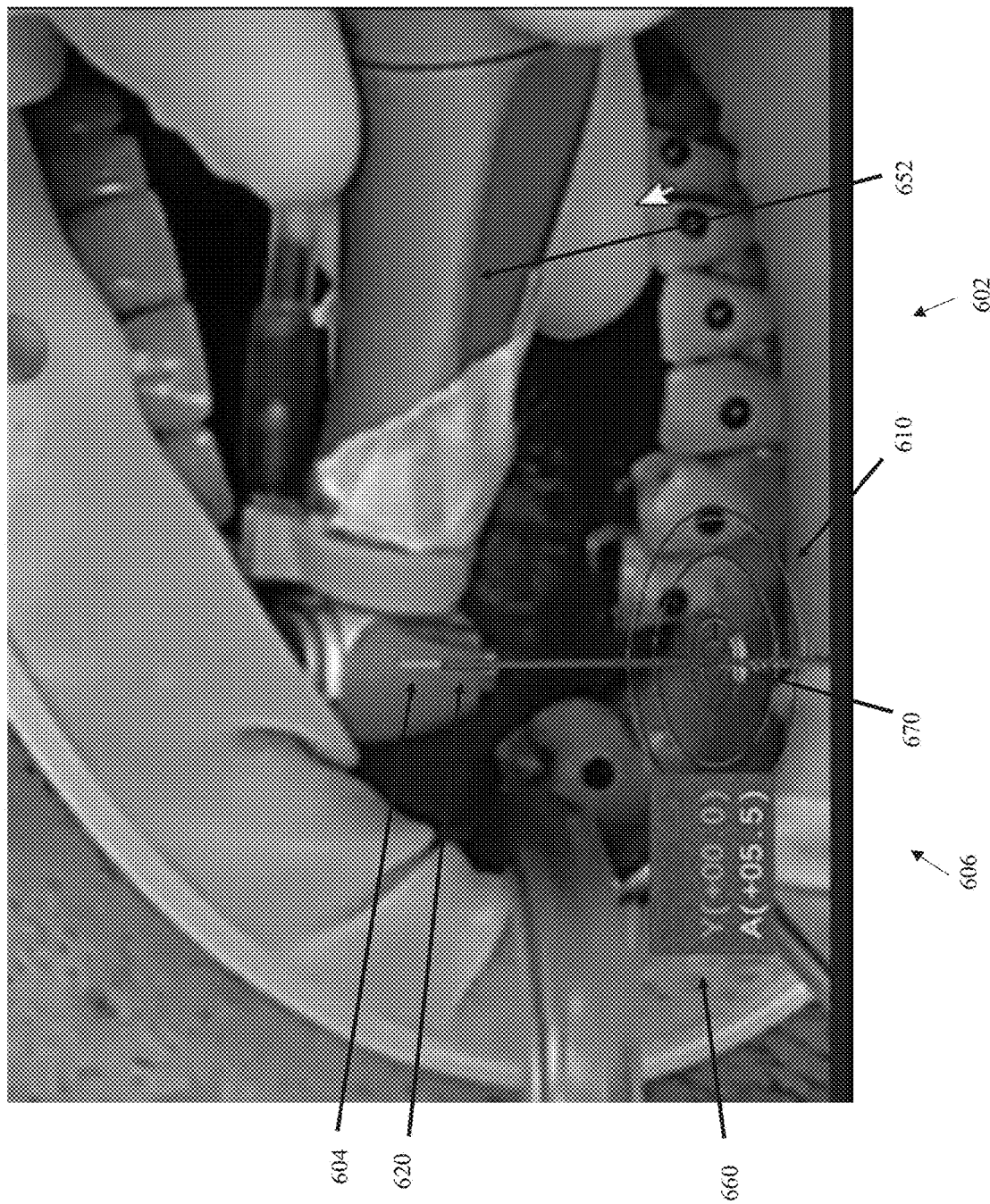
FIG. 6 is a schematic of an exemplary GUI depicting a small misalignment between a target virtual vector and a current virtual vector overlaid on a frame depicting an oral cavity of a subject, in accordance with some embodiments of the present invention.
Figure 7:
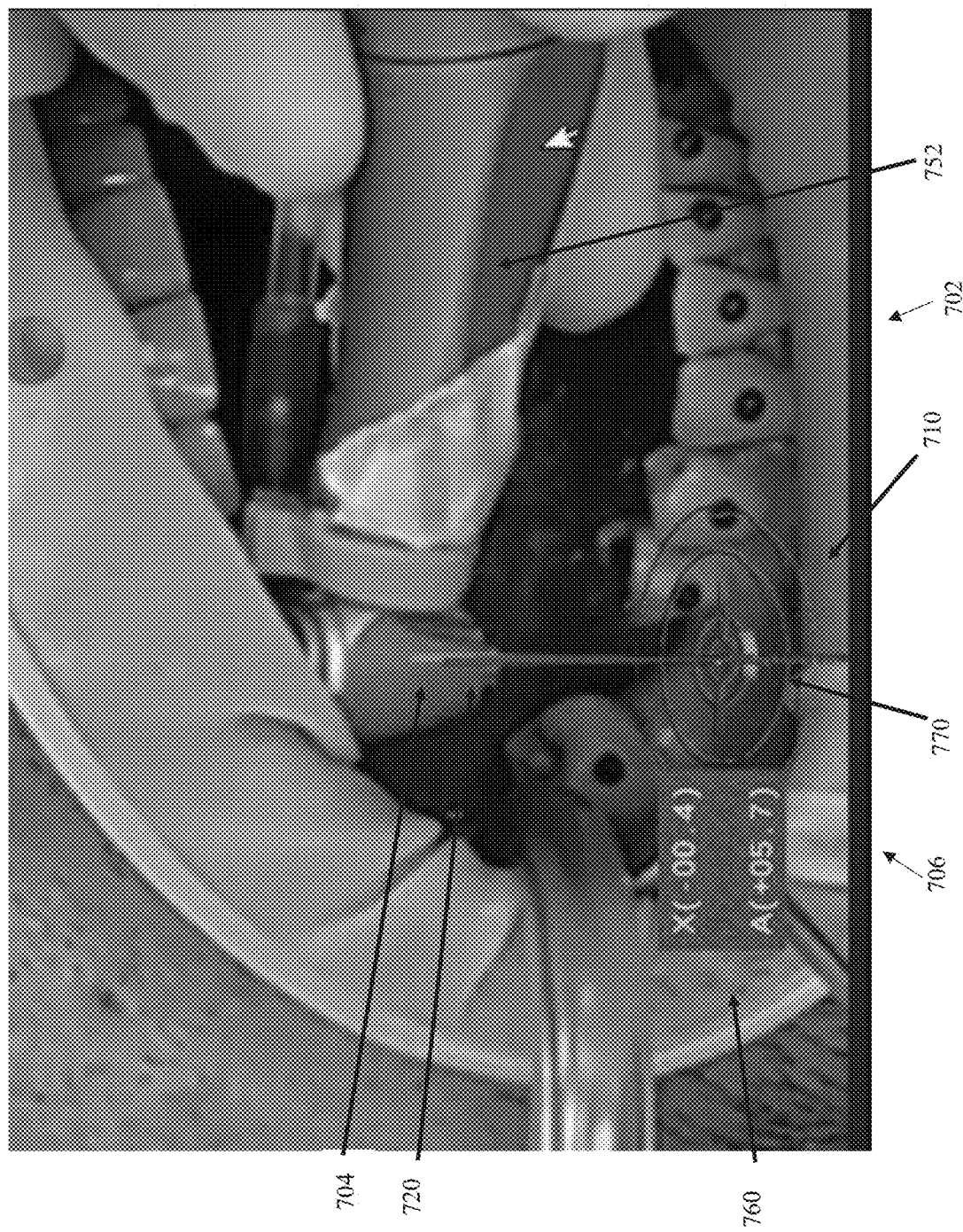
FIG. 7 is a schematic of an exemplary GUI depicting another small misalignment between a target virtual vector and a current virtual vector overlaid on a frame depicting an oral cavity of a subject, in accordance with some embodiments of the present invention.

Reference is now made to FIG. 1 which is a block diagram of components of a system 100 for creating and/or updating a GUI for guiding positioning of a dental implant in a subject, in accordance with some embodiments of the present invention. Reference is also made to FIG. 2, which is a flowchart of a method of creating and/or updating a GUI for guiding positioning of a dental implant in a subject, in accordance with some embodiments of the present invention. Reference is also made to FIG. 3, which is a schematic of an exemplary GUI 302 including a target virtual vector 304 overlaid on a frame 306 depicting an oral cavity of a subject, in accordance with some embodiments of the present invention. Reference is also made to FIG. 4, which is a schematic of an exemplary GUI 402 depicting a misalignment between a target virtual vector 404 and a current virtual vector 420 overlaid on a frame 406 depicting an oral cavity of a subject, in accordance with some embodiments of the present invention. Reference is also made to FIG. 5, which is a schematic of an exemplary GUI 502 depicting an alignment between a target virtual vector 504 and a current virtual vector 520 overlaid on a frame 506 depicting an oral cavity of a subject, in accordance with some embodiments of the present invention. Reference is also made to FIG. 6, which is a schematic of an exemplary GUI 602 depicting a small misalignment between a target virtual vector 604 and a current virtual vector 620 overlaid on a frame 606 depicting an oral cavity of a subject, in accordance with some embodiments of the present invention. Reference is also made to FIG. 7, which is a schematic of an exemplary GUI 702 depicting another small misalignment between a target virtual vector 704 and a current virtual vector 720 overlaid on a frame 706 depicting an oral cavity of a subject, in accordance with some embodiments of the present invention.

System 100 described with reference to FIG. 1 may implement the features of the method described with reference to FIG. 2, by one or more processors 102 of a computing environment 104 executing code instructions 106A stored on a memory 106.

Computing environment 104 may be implemented as, for example, a client terminal, a server, a virtual machine, a virtual server, a computing cloud, a mobile device, a desktop computer, a thin client, a Smartphone, a Tablet computer, a laptop computer, and an augmented reality device. Computing environment 104 may include an advanced visualization workstation that sometimes is add-on to a dentistry workstation and/or other devices.

Computing environment 104 may receive image(s) captured by image sensor(s) 112, process the images optionally using additional data (e.g., obtained from data storage device 152, repository of data 120A, and/or other sources), and generate a presentation (e.g., fused images and/or overlays) on a user interface 150, optionally an augmented reality presentation, as described herein.

Image sensor(s) 112 may be implemented as cameras capturing images in the visible light spectrum for example, CCD, CMOS sensors, and/or red green blue (RGB) sensor.

User interface(s) 150 may be implemented as an Augmented Reality (AR) display device, for example, a Head Mounted Display (HMD), AR goggles, and/or the like.

Alternatively or additionally, system 100 includes one or more accessory user interfaces 124, which may be in communication with computing environment 104. Accessory user interface(s) 124 may be used by a user, for example, to input data, such as select which internal anatomical structure of the subject to depict in an overlay over a visible light image of the oral cavity of the subject (e.g., nerves, jawbone, roots of teeth), as described herein. For example, accessory user interface(s) 124 may include the microphone and voice activated software to enable the user (e.g., dentist) to issue voice commands, such as for selecting what is presented within the GUI. Accessory user interface(s) 124 may be used, for example, for presenting additional data in addition to, and/or alternatively to, user interface 150. For example, fused and/or overlaid images presented within an AR display device may also be presented on a secondary display. In another example, CT scans, oral scans, and the like, which are not presented within the AR display may be presented on the secondary display. Accessory user interface(s) 124 may include, for example, one or more of: a touchscreen, a display screen, a keyboard, a mouse, and voice activated software using speakers and microphone.

Multiple architectures of system 100 based on computing environment 104 may be implemented:

In an exemplary implementation of a localized architecture, computing environment 104 may provide dedicated and/or localized services (e.g., one or more of the acts described with reference to FIG. 2), for example, to a dentist in a clinic. Computing environment 104 may be implemented within user interface 150, for example, within an AR device. In another example, computing environment 104 may be external to user interface 150, and in local communication with user interface 150, optionally over network 110, such as a local network, a wireless communication channel (e.g., short range), cables, and the like. For example, computing environment 104 is implemented as a dental workstation, a laptop, a desktop, and/or a server in a dental clinic. Computing environment 104 may locally obtain images from image sensors 112, generate the fused image(s) and/or overlay (e.g., as described herein), and provide the fused image(s) and/or overlay for presentation on user interface 150.

In an exemplary implementation of a centralized architecture, computing environment 104 may be implemented as one or more servers (e.g., network server, web server, a computing cloud, a virtual server) that provides centralized services (e.g., one or more of the acts described with reference to FIG. 2) to one or more interfaces 150 and/or client terminals 108 and/or servers 118 in communication with user interfaces 150 over a network 110, for example, providing software as a service (Saas), software services accessible using a software interface (e.g., application programming interface (API), software development kit (SDK)), an application for local download, and/or providing functions using a remote access session, such as through a web browser and/or viewing application. For example, computing environment 104 may be implemented as a server in a dental clinic, providing services to multiple client terminals 108 implemented as dental work stations located in multiple rooms. In each room, a dentist is wearing an AR device (e.g., user interview 150) which is in local communication with a respective dental work station. Images sensors 112 in each room send their images to the server (i.e., 104) over network 110 optionally vial their respective local client terminals 108. Fused images and/or overlays are centrally generated by the server, and sent over the network to respective work stations for local presentation on respective AR devices.

Image sensor(s) 112 may transmit captured images (e.g., of the oral cavity of a dental patient) to computing environment 104, for example, via a direct connected (e.g., local bus and/or cable connection and/or short range wireless connection), and/or via network 110 and a network interface 122 of computing environment 104 (e.g., where sensor(s) 112 are connected via internet of things (IoT) technology and/or are located remotely from the computing environment 104). In another implementation, images captured by sensor(s) 112 are sent to computing environment 104 via client terminal 108 and/or server 118 which may be in local communication with sensor(s) 112.

Network interface 122 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, application programming interface (API), software development kit (SDK), virtual network connection, a virtual interface implemented in software, network communication software providing higher layers of network connectivity).

Processor(s) 102 of computing environment 104 may be hardware processors, which may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include a single processor, or multiple processors (homogenous or heterogeneous) arranged for parallel processing, as clusters and/or as one or more multi core processing devices.

Memory 106 stores code instructions 106A executable by hardware processor(s) 102. Exemplary memories 106 include a random access memory (RAM), read-only memory (ROM), a storage device, non-volatile memory, magnetic media, semiconductor memory devices, hard drive, removable storage, and optical media (e.g., DVD, CD-ROM). For example, memory 106 stores code 106A that execute one or more acts of the method described with reference to FIG. 2.

Computing environment 104 may include a data storage device 120 for storing data, for example, a repository of data 120A that may store data as described herein, for example, CT images, 3D models, intraoral scan, and the like. Data storage device 120 may be implemented as, for example, a memory, a local hard-drive, a removable storage unit, an optical disk, a storage device, a virtual memory and/or as a remote server 118 and/or computing cloud (e.g., accessed over network 110).

Alternatively or additionally, computing environment 104 may be in communication (e.g., over a network 110) with one or more data storage devices 152 that may store data used herein, for example, CT images, 3D models, intraoral scan, and the like. Examples of data storage devices 152 include: data storage servers, cloud storage, external data storage devices, and the like.

Referring now back to FIG. 2, at 202, a target vector is presented within a GUI, over a frame of an oral cavity of a subject, optionally as an overlay.

The frame may be one of a sequence of frames. The frames may be captured by one or more image sensors (e.g., camera) during a dental session of the subject. For example, the frames are captured by a camera which may be located on an AR device worn by a user (e.g., dentist) during the dental session.

The terms frame and image may be used interchangeably. The frames may be 2D images.

The GUI, including the frames overlaid with one or more visual elements described herein, may be presented within the AR device worn by the user.

The target virtual vector may represent a target vector including a target location and/or a target angle for drilling by a real-world bur of a real-world drill for insertion of a dental implant.

The target virtual vector may be presented with respect to a 3D virtual model of a dental implant. For example, the user may select to present the 3D virtual model of the dental implant according to the target vector, such as to virtually illustrate how the dental implant is presented to look after being implanted at the location corresponding to the target virtual vector. The 3D virtual model of the dental implant may represent the implant portion that is inserted into the teeth and/or the dental prosthesis that connects to the implant, such as the crown.

The target virtual vector may be a virtual vector that is fixed after being manipulated in response to a real-world location and/or a real-world angle of a tool (optionally the real-world drill with bur) being manipulated by a user. Exemplary details of creating and/or updating a GUI, optionally presented within the AR device, for adapting a virtual location and/or virtual angle of the virtual vector, and defining the target virtual vector by fixing the virtual vector at the target virtual location and/or target virtual angle corresponding to the real-world location and/or real-world angle of the drill within the oral cavity of the subject, are described, for example, with reference to co-filed U.S. Patent Application entitled "INTERACTIVE VISUALIZATION OF DENTAL IMPLANT POSITION PLANNING" (Ser. No. 18/656,633), the contents of which are incorporated herein by reference in their entirety.

Alternatively or additionally, the target virtual vector may be automatically computed based on anatomical landmarks identified within the oral cavity and a set of rules applied to distances to the anatomical landmarks. The anatomical landmarks may be automatically detected as follows: the frame(s) may be registered to a dental 3D imaging model. The dental 3D imaging model may be created based on a 3D scan of the oral cavity of the subject, which may be captured pre-procedure, for example, a CT scan and/or MRI scan. The anatomical landmarks may be identified within the 3D scan and/or the dental 3D imaging model, for example, automatically by one or more detector models and/or manually by a user. The anatomical landmarks may include structures below a surface of the oral cavity, which cannot be seen visually by a human looking into the subject's mouth. The registration enables mapping the locations of the anatomical landmarks identified on the dental 3D imaging model to the 2D frame. The 2D frame may be registered to the dental 3D imaging model, for example, by substantially matching a pattern of intraoral markers which may be positioned on the teeth of the subject during the 3D scan and during capture of the frames. In another example, teeth of the subject may be segmented from the 2D frame and from the dental 3D imaging model, and registration is performed between the segmented teeth.

Additional exemplary details of registration between frames and the dental 3D imaging model are described, for example, with reference to International Patent Application Publication No. WO2022/190105, entitled "ENHANCING DENTAL VIDEO TO CT MODEL REGISTRATION AND AUGMENTED REALITY AIDED DENTAL TREATMENT", filed on Mar. 10, 2022, incorporated herein by reference in its entirety.

The anatomical landmarks may include structures to avoid drilling into, for example, nerves and/or tooth roots. The distance from the target virtual vector to the structures to avoid may be computed. The set of rules may define a threshold indicating a minimal distance to maintain between the bur during drilling and the structure to avoid. Alternatively or additionally, the anatomical landmarks may include locations relative to where the implant is to be positioned, for example, the jawbone (e.g., anatomical locations of the jawbone), and/or specific teeth. The distances and/or directions may be from the anatomical landmarks. The set of rules may define where to drill using the distances and/or directions. For example, distance and/or location from arc of the jaw, between two specific teeth.

The target virtual vector is presented as an overlay on the frame, within the GUI. The target virtual vector may be presented as a line. The line is parallel to a direction for drilling for insertion of the dental implant. The length of the line may correspond to a length of the bur, and/or may be selected to be visually clear to the user, such as long enough to have one portion within tissue and another portion external to tissue. A region (e.g., center) of the line may correspond to an initial location for drilling. The target virtual vector may include multiple other visual elements arranged along plane, optionally two or more concentric circles. The line may be normal to the plane of the visual elements. The region of the line indicating the initial location for drilling may be positioned at a center of the visual elements (e.g., concentric circle). The center of the visual elements may correspond to the initial location for drilling. The line may be positioned relative to the visual elements such that one portion of the line below the region is depicted within tissue and the other portion of the line above the region is depicted external to the tissue.

At 204, a real-world location and/or real-world angle of the real-world bur of the drill during manipulations by a user is monitored and/or computed.

It is to be understood that other real-world structures corresponding to the bur and/or drill may be monitored, and a mapping may be used to map to the bur and/or drill.

The real-world location and/or angle may be dynamically computed in response to manipulations by the user, for example, displacement in 3D space, and/or change in angle. It is noted that change in rotation is not necessarily computed, based on the assumption that the drill bit rotates for drilling, and determination of rotation is not relevant.

The drill may be for use by a user (e.g., dentist) for drilling into the jaw, for inserting the dental implant. The location may be defined according to a tip of a bur of the drill. The angle may be defined between the bur of the drill and a plane parallel to an x-y plane of a coordinate system of the frames, at a pivot point defined by the tip of the bur.

The real-world location and/or angle may be computed within the coordinate system of the frames. The coordinate system may be common to the target virtual vector and the bur of the drill.

The real-world location and/or angle of the real-world tool may be computed using different approaches. For example, in one approach, outputs of one or more pose sensors installed on the tool is analyzed to obtain the pose of the tool. In another example, predefined features of the real-world tool are extracted from the 2D frame. The predefined features may be matched to corresponding predefined features of a 3D model of the tool which may be set a baseline pose, such as aligned along one or more axes. The location and/or angle of the tool may be computed based on a translation from the predefined features extracted from the 2D frame to the predefined features of the 3D model. In yet another example, one or more predefined markers having a known baseline pose are connected to the tool. The predefine markers are detected on the 2D frame. The location and/or angle of the tool may be computed based on a translation from the pose of the markers extracted from the 2D frame to the known baseline pose.

The real world location of the jaw and/or other anatomical structures may be computed. The real world location of the jaw and/or other anatomical structures may be computed based on a detection of the teeth in the image (e.g., by a detector model, a segmentation model, and/or by detecting intraoral markers placed on the teeth), and registering the teeth to a dental 3D imaging model of the teeth (e.g., acquired from the 3D image, such as a CT scan). The registration may be performed, for example, based on a simultaneous localization and mapping (SLAM) approach by solving the estimation of the pose of the camera on the AR device, and obtaining a MVP (model-view-projection) matrix which translates the location of the model (e.g., jaw) to the camera space. An analogous may be computed for the drill, which may be detected (e.g., by a detector model, a segmentation model, and/or by detecting one or more features and/or markers), registering the drill with a corresponding 3D model (e.g., acquired by 3D scanning the drill during a pre-procedure calibrations process) and solving its MVP model view projection matrix with SLAM. The outcome of having each model (e.g., jaw, drill) at each frame and a corresponding updated model view matrix for each model, selected locations may be projected from a certain coordinate space of each of the model to the common camera coordinate space (e.g., denoting the real world). Distances may be measured within the common camera coordinate space, for example, the distance from the tip of the bur of the drill to the nerve.

It is noted that the real-world location is optional, since other data for implementing features described herein may be extracted and/or computed based on the coordinate space of the camera (e.g., corresponding to the real world). The AR device's spatial awareness feature may be used to track the location and/or movement of the camera in the real world in order to remove estimated movement that may be a possible solutions in the SLAM but do not correlate with the boundaries of the spatial awareness of the AR device and as a result get better more optimal SLAM performance.

Optionally, the frames are registered to the coordinate system, and the real-world location and/or angle of the tool is computed relative to the coordinate system. The frames may be registered to the coordinate system by defining the coordinate system relative to the dental 3D imaging model of the subject that includes anatomical features relates to the oral cavity, for example, a CT scan and/or MRI scan. The coordinate system may represent real-world measurements based on the dental 3D imaging model. The location and/or angle of the tool may be defined within the coordinate system defined based on the dental 3D imaging model.

At 206, a current virtual vector including a virtual location and/or virtual angle is computed.

The current virtual vector corresponds to a current value of the monitored and/or computed real-world location and/or real-time angle of the real-world bur of the drill.

The current virtual vector may be defined within the coordinate system in which the target virtual vector is defined. The virtual location and/or virtual angle of the current virtual vector within the coordinate system corresponds to the real-world location and/or real-world angle of the bur of the drill.

The current virtual vector is presented as an overlay on the frame, within the GUI. The overlay may be the same as the overlay presenting the target virtual vector, or may be a different overlay than the overlay presenting the target virtual vector. The current virtual vector may be simultaneously presented with the target virtual vector. The current virtual vector may be presented as a line. The line may be parallel to a long axis of the bur. The length of the line may correspond to a length of the bur, and/or may be selected to be visually clear to the user, such as long enough to have one portion within tissue and another portion external to tissue. The length of the line indicating the current virtual vector may substantially match the length of the line denoting the target virtual vector. A region (e.g., center) of the line may correspond to a tip of the bur. The current virtual vector may include multiple other visual elements arranged along plane, optionally two or more concentric circles. The line may be normal to the plane of the visual elements. The region of the line indicating the tip of the bur may be positioned at a center of the visual elements (e.g., concentric circle). The center of the visual elements may correspond to the tip of the bur. The line may be positioned relative to the visual elements such that one portion of the line below the region is depicted within tissue and the other portion of the line above the region is depicted external to the tissue.

At 208, a misalignment between the current virtual vector and the target virtual vector is computed and/or tracked. The misalignment may include one or more of the following:

Misalignment in terms of location between the current virtual vector and the target virtual vector. The misalignment may be computed between the tip of the current virtual vector and the tip of the target virtual vector. The misalignment may be defined along three axes, such as displacement along a 2D plane defined by the x-axis and y-axis, and/or an elevation displacement along a z-axis.

Misalignment in terms of angle, between the angle of the current virtual vector and the angle of the target virtual vector. Each angle may be defined between the line and a plane that represents a tangent to the surface of the tissue that intersects the line, representing the initial location for drilling.

Misalignment in terms of depth between the location of the current virtual vector corresponding to a tip of the bur (e.g., distal tip of the line indicating the current virtual vector), and the initial location for drilling (e.g., surface of the jawbone where) defined by the target virtual vector. Alternatively the misalignment may be between the location of the current virtual vector corresponding to the tip of the bur and a portion of the target virtual vector indicating maximum depth for drilling.

The misalignment may be for the current virtual vector relative to the target virtual vector. The misalignment may indicate how to adapt the current virtual vector for alignment with the target virtual vector.

An indication of the misalignment may be presented within the GUI as an overlay over the frame. For example, distance to move along the x, y, and/or z axes to align the tip of the bur with the target virtual vector, and/or amount of angular rotation to perform to align the long axis of the bur with the line representing the target virtual vector and/or amount of depth (e.g., from the initial location of drilling and/or to the maximum depth).

It is noted that alignment may be determined as being achieve when the current virtual vector and the target virtual vector are aligned along the x-axis and/or y-axis, where location along the z-axis is at the level from the initial location for drilling and below. I.e., depth may be variable while alignment is maintained, indicating drilling is in progress at the target location and/or target angle.

At 210, the GUI is dynamically updated in response to the misalignment.

Optionally, an indication for reducing the misalignment for obtaining an alignment between the current virtual vector and the target virtual vector is presented within the GUI. The indication for reducing the misalignment may be dynamically updated according to the misalignment dynamically computed based on real-time values of the current virtual vector.

The indication for reducing the misalignment may be for adapting spatial coordinates of the current virtual vector to match the spatial coordinates of the target virtual vector, and/or for adapting the angle of the current virtual vector to substantially match the angle of the target virtual vector. The adaptation may be performed by the user, by adjusting their hand to move and/or orient the drill.

The indication may be, for example, a presentation of offset of the current virtual vector from the target virtual vector. The offset may be presented as numerical values and/or text. The offset may indicate the distance to displace the current virtual vector to align with the target virtual vector, optionally along the x-axis and/or y-axis and/or z-axis. The distance may be, for example, in pixels, in millimeters, or other values. The offset may indicate the amount of angular rotation (optionally using the point of the bur as the pivot point) to align the current virtual vector with the target virtual vector. The offset may be visually coded (e.g., color, pattern, bolding) to indicate directions, such as up-down, left-right, forward-backwards, tilt up-down.

When misaligned, the current virtual vector and the target virtual vector are presented as two distinct lines and/or visual elements. The lines and/or visual elements may overlap according to the amount of misalignment. When aligned, the current virtual vector and the target vector substantially overlap each other, appearing as a single vector. It is noted that the alignment presented within the GUI may not be 100% even when the current virtual vector and the target virtual vector may be determined to be aligned, due for example, to natural small movements of the hand of the use holding the drill, and/or resolution of the vectors. The alignment may be determined within a range, for example, about 1 millimeter or about 2 millimeters, and/or within about 5 degrees or 10 degrees.

Alternatively or additionally, the indication for reducing misalignment may be presented as a marker presented with respect to the visual elements and/or line representing the current virtual vector. The marker may be designed to visually indicate the adaption for alignment with the target visual vector. The visual marker may be different than the numerical values and/or text. For example, a location and/or shape and/or color of the marker is selected with respect to the visual elements and/or line, for indicating a direction and/or amount and/or angle for adapting the current virtual vector for alignment with the target virtual vector. For example, in the implementation of the visual elements as two or more concentric circles, the marker may be presented as a thickened and/or colored arc portion of the concentric circles. For example, the marker may be one or more of: a color, a certain arc length, and a specific concentric circle of the multiple concentric circles. The location of the marker along the circle may indicate the direction to displace the current visual vector for alignment with the target visual vector. The color and/or arc length of the marker may indicate, for example, amount of displacement, such as large, medium, large, where the color and/or arc length changes as the misalignment is reduced. The marker may be positioned along a specific concentric circle of the multiple concentric circles according to a magnitude of the misalignment between the current virtual vector and the target virtual vector. For example, positioning the marker at a relatively outer concentric circle may indicate a relatively larger magnitude for reducing misalignment. Positioning the marker at a relatively inner concentric circle may indicate a relatively smaller magnitude for reducing misalignment.

Alternatively or additionally, the indication for reducing misalignment may be presented as an adaptation vector indicating a magnitude and/or direction for adapting the location of the current virtual vector for alignment with a location of the target virtual vector. The adaption vector may be presented as a line connecting a position of the current virtual vector optionally corresponding to a tip of the bur, and a position of the target virtual vector optionally corresponding to an initial location for drilling. The color and/or pattern of the line indicating the adaptation vector may be different than the color and/or pattern of the lines representing the current virtual vector and/or the target virtual vector. The line may visually represent a rubber band, which dynamically expands when the misalignment increases, and dynamically contracts when the misalignment decreases.

Alternatively or additionally, the indication may be of depth relative to the target virtual location, optionally depth of the tip of the bur relative to the initial location for drilling which may be located at the surface of the jaw. The depth of the tip of the bur may be dynamically tracked and presented. The depth may be presented while the long axis of the bur is aligned with the angle and/or location of the target virtual vector, indicating that drilling is occurring at the correct location.

At 212, the GUI may be dynamically updated based on one or more features described with reference to 202-210.

The GUI may be dynamically updated by dynamically adapting the virtual location and/or the virtual angle of the current virtual vector overlaid on the frame, which may simultaneously present the target virtual vector.

The GUI may be presented within an augmented reality device worn by the user, optionally the dentist.

The GUI may be updated according to the pose of the head of the user wearing the augmented reality device and/or according to the pose of the head of the subject undergoing the dental implant procedure, according to the registration between the frame and the dental 3D imaging model, and/or according to the pose of the camera within the coordinate system. For example, the target virtual vector fixed with respect to a certain gap between existing teeth is dynamically updated as the user changes the pose of their head, and/or as the subject changes the pose of their head, relative to the camera capturing the frames.

The GUI may include one or dental-related anatomical structures of the subject, which may include structures to avoid during drilling and/or structures being drilled into. For example, a jawbone, nerves, and teeth roots. The dental-related anatomical structures may be obtained by segmentation of the dental-related anatomical structure from a dental 3D imaging model registered to the frame. The dental 3D imaging model may be created from a 3D image, for example, a CT scan and/or MRI scan. A fused frame including the segmented dental-related anatomical structure fused with the frame may be created. The current virtual vector and/or target virtual vector and/or indication(s) of misalignment may be presented within the GUI as overlays over the fused frame. Additional exemplary details of creating fused frames are described, for example, with reference to International Patent Application Publication No. WO2022/190105, entitled "ENHANCING DENTAL VIDEO TO CT MODEL REGISTRATION AND AUGMENTED REALITY AIDED DENTAL TREATMENT", filed on Mar. 10, 2022, and/or co-filed U.S. Patent Application entitled "INTERACTIVE VISUALIZATION OF DENTAL IMPLANT POSITION PLANNING" (Ser. No. 18/656,633), the contents of which are incorporated herein by reference in their entirety.

This application is also related to incorporated herein by reference in its entirety At 214, a stage during the procedure for insertion of the dental implant may be detected. Example stages include: prior to the drill being located at the target location for drilling, drill location at the target location for drilling, start of drill, drilling stage, active drilling, termination of active drilling, and implant placement.

The stage may be automatically detected, for example, based on an analysis of the misalignment and/or location of the current virtual vector. For example:

A misalignment in terms of displacement in space along the x-axis and/or y-axis indicates the stage prior to drilling.

Alignment of the current vector with the target vector may indicate the start of drilling.

A change in depth while maintaining alignment with respect to the angle and/or location along the x-axis and/or y-axis may indicate the drilling stage.

Absence of the drill and detection of the implant (e.g., being maneuvered by the use) indicates implant placement.

Alternatively, the stage may be manually set, such as by a user speaking into a microphone associated with voice recognition software, and/or pressing an icon on a display, and the like.

A presentation protocol of the GUI indicating features for presentation within the GUI may be set according to the stage. The presentation protocol may be defined for different users, for example, based on personal preferences. For example:

In response to detecting drilling by the drill, terminating the presentation of the target virtual vector (e.g., overlay) and of the current virtual vector, which may enable the user to more clearly visualize the drill without obstruction by the overlays.

In response to detecting termination of drilling by the drill. The target virtual vector and the current virtual vector may be re-presented, which may assist the user in checking alignment without risking damage to tissue (since the bur is not spinning).

When the drill is not located at the target location, an indication of misalignment may be presented. The misalignment may include an indication of misalignment in space along the x-axis and/or y-axis, and optionally the z-axis, and/or the angle misalignment, which may assist the user in maneuvering the drill to the target location. Depth may be excluded from the presentation, since depth is not relevant until drilling has begun.

During drilling and/or during implant placement, the depth of the current virtual vector which may correspond to the tip of the bur, may be presented. The angle, and/or misalignment in terms of the angle, may also be presented simultaneously with the depth. Other information, such as coordinates in space may be omitted. The angle may be used for maintaining alignment during drilling. The depth may be used to determine when to stop the drilling. The location in space may be irrelevant during drilling, since the drill is at the correct location.

In response to detecting implant placement, the monitoring may switch from the drill to the implant. The current virtual vector may correspond to the implant, switching from the drill.

During implant placement, the depth of the implant may be tracked and presented (since the drill is no longer being used). The depth of the implant may be presented relative to the surface of the jawbone, to help the user determine whether the implant is being placed at the correct depth.

At 216, one of more features described with reference to 202-214 may be iterated. Each iteration may be performed for one frame of the sequence of frames.

Referring now back to FIG. 3, GUI 302 includes target virtual vector 304 overlaid on frame 306 depicting an oral cavity of a subject. Target virtual vector 304 may include a line 308 and two or more concentric circles 310. Line 308 may pass through a center of concentric circles 310. Line 308 may be a normal to a plane along which concentric circles 310 lie. A 3D model of a dental implant 312 may be presented within GUI 302, positioned according to target virtual vector 304. A first portion 308A of line 308 external to dental implant 312 may be shown as continuous. A second portion 308B of line 308 internal and below dental implant 312 may be shown as dotted/dashed.

Referring now back to FIG. 4, GUI 402 presents target virtual vector 404 and current virtual vector 420 overlaid on frame 406 depicting an oral cavity of a subject. A location and/or angle of current virtual vector 420 corresponds to a real-world location and/or real-world angle of a bur of a drill 452 being manipulated by a user. Drill 452 is to be used for drilling into a jaw of the subject for insertion of the dental implant.

Current virtual vector 420 may include a line 408 and two or more concentric circles 410. Line 408 may pass through a center of concentric circles 410. Line 408 may be a normal to a plane along which concentric circles 410 lie. A first portion 408A of line 408 above the plane of concentric circles 410, optionally above the surface of tissues, may be shown as continuous. A second portion 408B of line 408 below the plane of concentric circles 410, optionally below the surface of tissues, may be shown as dotted/dashed.

GUI 402 may further present one or more indications of a misalignment between target virtual vector 404 and current virtual vector 402. The indication of misalignment may be visually presented as a line 450 connecting virtual vector 404 and current virtual vector 402, optionally connecting the center of concentric circles. Line 450 may represent a vector indicating to the user to where to maneuver the tip of the bur of drill 452.

GUI 402 may further present numerical values 460 indicating displacement in space, along x and y (optionally z) axes defining a coordinate system and/or an angle, of the misalignment between target virtual vector 404 and current virtual vector 402. As shown, the tip of the bur is displaced from the target location for drilling defined by the target vector, +94.5 along the x-axis, +11.0 along the y axes, and an angle of +14.2. Components (e.g., along an axes and/or the angle) that are misaligned may be color coded accordingly, for example, in red.

Referring now back to FIG. 5, GUI 502 depicts the alignment between target virtual vector 504 and current virtual vector 520 overlaid on frame 506 depicting an oral cavity of a subject. Alignment is indicated by the substantial overlap between target virtual vector 504 and current virtual vector 520.

Alignment may be further indicated by numerical values 560 that are close to zero. Numerical values 560 indicate displacement in space, along x and y (optionally z) axes defining a coordinate system and/or an angle, of the misalignment between target virtual vector 504 and current virtual vector 502. The alignment indicates that a bur of a drill 552 is correctly positioned for drilling. Components (e.g., along an axes and/or the angle) that are aligned may be color coded accordingly, for example, in green.

GUI 502 may present one or more dental-related anatomical structures, which may be obtained from a segmentation of the dental-related anatomical structure(s) of the subject segmented from a dental 3D imaging model registered to the frame (e.g., CT scan, MRI scan). In the depicted example, the dental-related anatomical structure includes nerves 570A-B, which are to be avoided during drilling.

Referring now back to FIG. 6, GUI 602 depicts the small misalignment between target virtual vector 604 and current virtual vector 620 overlaid on frame 606 depicting an oral cavity of a subject. The small misalignment is presented within numerical values 660 as a misalignment of the angle of +5.5. A marker 670, presented along a circle of concentric circles 610 of the virtual vector and/or the current vector, indicating the direction and/or magnitude of the manipulation of a drill 652 to be performed by the user.

Referring now back to FIG. 7, GUI 702 depicts the small misalignment between target virtual vector 704 and current virtual vector 720 overlaid on frame 706 depicting an oral cavity of a subject. The small misalignment is presented within numerical values 760 as a misalignment along the y-axis of −2.4. A marker 770, presented along a circle of concentric circles 710 of the virtual vector and/or the current vector, indicating the direction and/or magnitude of the manipulation of a drill 752 to be performed by the user.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant GUIs will be developed and the scope of the term GUI is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method for processing data using at least one processor coupled to a memory, the method comprising:
   displaying via a display unit of a client computing device, an interactive graphical user interface (GUI) for guiding positioning of a dental implant in a subject;
   presenting within the GUI, a first overlay of a target virtual vector overlaid on at least one image of an oral cavity of a subject captured by at least one image sensor during a dental session of the subject,
   wherein the target virtual vector denotes a target vector defining a target location and a target angle for drilling by a real-world bur of a real-world drill for insertion of a dental implant;
   monitoring a real-world location and angle of the real-world bur of the drill during manipulations by a user; and
   dynamically updating, within the GUI, a second overlay of a current virtual vector overlaid on the at least one image including the first overlay, the current virtual vector including a virtual location and virtual angle corresponding to a current value of the monitored real-world location and angle of the real-world bur of the drill,
   wherein the current virtual vector is presented as a first line parallel to a long axis of the bur and as a plurality of first concentric circles arranged along a first plane, the first line is normal to the first plane, the target virtual vector is presented as a second line parallel to a direction for drilling for insertion of the dental implant and as a plurality of second concentric circles arranged along a second plane, the second line is normal to the second plane,
   wherein when misaligned the plurality of first concentric circles and the plurality of second concentric circles are distinct and dynamically visually adapted for indicting direction and/or amount and/or angle for alignment, and when aligned are depicted as a single set of concentric circles.

2. The computer-implemented method of claim 1, further comprising computing the target virtual vector based on anatomical landmarks identified within the oral cavity and a set of rules applied to distances to the anatomical landmarks.

3. The computer-implemented method of claim 1, further comprising dynamically tracking a misalignment between the current virtual vector and the target virtual vector, and presenting within the GUI, an indication of the misalignment.

4. The computer-implemented method of claim 3, further comprising presenting within the GUI, an indication for reducing the misalignment for obtaining an alignment between the current virtual vector and the target virtual vector.

5. The computer-implemented method of claim 3, wherein the indication for reducing the misalignment is for adapting at least one of: spatial coordinates of the current virtual vector to match the spatial coordinates of the target virtual vector, the angle of the current virtual vector to substantially match the angle of the target virtual vector, and a depth of the current virtual vector corresponding to a tip of the tool relative to an initial location for drilling defined by the target virtual vector.

6. The computer-implemented method of claim 3, further comprising computing a value indicating the amount of misalignment presenting an alert within the GUI when the value is larger than a threshold.

7. The computer-implemented method of claim 1.

8. The computer-implemented method of claim 1, wherein a center of the plurality of first concentric circles and a center of the first line correspond to a tip of the bur.

9. The computer-implemented method of claim 8, wherein a center of the plurality of second concentric circles corresponds to an initial location for drilling, wherein a center of the second line corresponds to the initial location for drilling, wherein a first portion of the second line below the center is depicted within tissue and a second portion of the second line above the center is depicted external to the tissue.

10. The computer-implemented method of claim 9, further comprising:
dynamically computing an adaption of the current virtual vector for alignment with the target virtual vector; and
visually presenting within the GUI a marker with respect to the plurality of first visual elements indicating the adaption for alignment.

11. The computer-implemented method of claim 10, wherein a location and/or shape and/or color of the marker with respect to the plurality of first visual elements indicates a direction and/or amount and/or angle for adapting the current virtual vector for alignment with the target virtual vector.

12. The computer-implemented method of claim 1, wherein dynamically visually adapted comprises a thickened and/or colored arc portion of the plurality of concentric circles, and at least one of: a color, length, a specific concentric circle of the plurality of concentric circles, visually indicates the direction and/or amount and/or angle for adapting the current virtual vector for alignment with the target virtual vector.

13. The computer-implemented method of claim 12, wherein the specific concentric circle of the plurality of first and second concentric circles is dynamically adapted according to a magnitude of the misalignment between the current virtual vector and the target virtual vector, wherein a relatively outer concentric circle indicates a relatively larger magnitude and a relatively inner concentric circle indicates a relatively smaller magnitude.

14. The computer-implemented method of claim 1, further comprising:
dynamically computing an adaptation vector indicating a magnitude and/or direction for adapting the location of the current virtual vector for alignment with a location of the target virtual vector; and
dynamically updating the adaption vector according to monitored changes in location of the current virtual vector.

15. The computer-implemented method of claim 14, wherein the adaption vector is presented as a distance to move along an x-axis, a y-axis, and an amplitude, from the current location of the virtual vector to the location of the target virtual vector.

16. The computer-implemented method of claim 14, wherein the adaption vector is presented as a line connecting a position of the current virtual vector corresponding to a tip of the bur, and a position of the target virtual vector corresponding to an initial location for drilling.

17. The computer-implemented method of claim 1, further comprising:
in response to detecting drilling by the drill, terminating the first overlay and the second overlay; and
in response to detecting termination of drilling by the drill, re-presenting the first overlay and the second overlay.

18. The computer-implemented method of claim 1, further comprising:
detecting a stage of during a procedure for insertion of the dental implant; and
setting a presentation protocol of the GUI indicating features for presentation within the GUI according to the stage.

19. The computer-implemented method of claim 18, further comprising:
detecting the stage according to a presence of the dental implant and absence of the drill within the at least one image,
monitoring the real-world location and/or angle of a real-world dental implant instead of the drill,
wherein the current virtual vector includes the virtual location and/or virtual angle corresponding to a current value of the monitored real-world location and/or angle of the real-world dental implant.

20. The computer-implemented method of claim 1, wherein the GUI including first overlay and the second overlay is presented over the at least one image within an augmented reality device worn by a user.

21. A system for presenting an interactive graphical user interface (GUI) for guiding positioning of a dental implant in a subject, comprising:
at least one processor executing a code for:
presenting a first overlay of a target virtual vector overlaid on at least one image of an oral cavity of a subject captured by at least one image sensor during a dental session of the subject,
wherein the target virtual vector denotes a target vector defining a target location and a target angle for drilling by a real-world bur of a real-world drill for insertion of a dental implant;
monitoring a real-world location and angle of the real-world bur of the drill during manipulations by a user; and
dynamically updating a second overlay of a current virtual vector overlaid on the at least one image including the first overlay, the current virtual vector including a virtual location and virtual angle corresponding to a current value of the monitored real-world location and angle of the real-world bur of the drill,
wherein the current virtual vector is presented as a first line parallel to a long axis of the bur and as a plurality of first concentric circles arranged along a first plane, the first line is normal to the first plane, the target virtual vector is presented as a second line parallel to a direction for drilling for insertion of the dental implant and as a plurality of second concentric circles arranged along a second plane, the second line is normal to the second plane,
wherein when misaligned the plurality of first concentric circles and the plurality of second concentric circles are distinct and dynamically visually adapted for indicting direction and/or amount and/or angle for alignment, and when aligned are depicted as a single set of concentric circles.

22. A non-transitory medium storing program instructions for presenting an interactive graphical user interface (GUI) for guiding positioning of a dental implant in a subject, which when executed by at least one processor, cause the at least one processor to:
  present a first overlay of a target virtual vector overlaid on at least one image of an oral cavity of a subject captured by at least one image sensor during a dental session of the subject,
    wherein the target virtual vector denotes a target vector defining a target location and a target angle for drilling by a real-world bur of a real-world drill for insertion of a dental implant;
  monitor a real-world location and angle of the real-world bur of the drill during manipulations by a user; and
  dynamically update a second overlay of a current virtual vector overlaid on the at least one image including the first overlay, the current virtual vector including a virtual location and virtual angle corresponding to a current value of the monitored real-world location and angle of the real-world bur of the drill,
  wherein the current virtual vector is presented as a first line parallel to a long axis of the bur and as a plurality of first concentric circles arranged along a first plane, the first line is normal to the first plane, the target virtual vector is presented as a second line parallel to a direction for drilling for insertion of the dental implant and as a plurality of second concentric circles arranged along a second plane, the second line is normal to the second plane,
  wherein when misaligned the plurality of first concentric circles and the plurality of second concentric circles are distinct and dynamically visually adapted for indicting direction and/or amount and/or angle for alignment, and when aligned are depicted as a single set of concentric circles.

* * * * *